United States Patent
Kim

[19]

[11] Patent Number: 6,074,410

[45] Date of Patent: Jun. 13, 2000

[54] FINGER-PRESSURE FUNCTIONING HEALTH-AID INSTRUMENT FOR IMPROVING BLOOD CIRCULATION IN THE HUMAN BODY

[76] Inventor: Chi-Kyung Kim, #8-301, Samseong Villa 173 Saugil-dong, Kangdong-ku, Seoul 135 080, Rep. of Korea

[21] Appl. No.: 09/020,763

[22] Filed: Feb. 9, 1998

Related U.S. Application Data

[63] Continuation of application No. PCT/KR96/00169, Oct. 2, 1996.

[30] Foreign Application Priority Data

Jun. 7, 1996 [KR] Rep. of Korea ....................... 96-15073

[51] Int. Cl.[7] .................................................. A61N 21/00
[52] U.S. Cl. .............................. 607/88; 607/96; 606/189; 606/204
[58] Field of Search ................................... 607/1, 88, 96; 606/189, 204; 128/907; 604/304

[56] References Cited

FOREIGN PATENT DOCUMENTS

| 1069897 | of 0000 | China . |
|---|---|---|
| 1098947 | of 0000 | China . |
| 1099258 | of 0000 | China . |
| 1107684 | of 0000 | China . |
| 1125596 | of 0000 | China . |
| 1135362 | of 0000 | China . |
| 0676186 | 10/1995 | European Pat. Off. . |
| 2417295 | 9/1979 | France . |
| 3227505 | 1/1984 | Germany . |
| 2014058 | 6/1994 | Russian Federation . |
| 2055609 | 3/1996 | Russian Federation . |
| 1301402 | 4/1987 | U.S.S.R. . |
| 1572626 | 6/1990 | U.S.S.R. . |
| 9524170 | of 0000 | WIPO . |

*Primary Examiner*—Linda C. M. Dvorak
*Assistant Examiner*—Roy Gibson
*Attorney, Agent, or Firm*—Baker Botts L.L.P.

[57] ABSTRACT

A finger-pressure functioning health-aid instrument for improving blood circulation of a human body includes a cylindrical body, and a lower cap, inserted in the lower part of the body. A negative ion discharge element is fixed within the body. A bio-ceramic is formed within the body and surrounds the upper and outer part of the negative ion discharge element. A permanent magnet is fixed under the negative ion discharge element and a pressure member is fixed contacting the lower face of the permanent magnet, and contacts directly with the skin in the desired treatment area and projects anions and emitting rays.

9 Claims, 3 Drawing Sheets

FINGER-PRESSURE FUNCTIONING HEALTH-AID INSTRUMENT FOR IMPROVING BLOOD CIRCULATION IN THE HUMAN BODY

This application is a continuation of PCT/KR96/00196 filed Oct. 2, 1996.

FIELD OF THE INVENTION

The present invention relates to a health aid instrument for improving blood circulation in the human body, and more particularly, to a finger-pressure functioning medical instrument for improving blood circulation which, by artificially projecting to specific areas far infrared rays, magnetic force rays, anions, etc., which are beneficial to the human body, promotes circulation in the body and, by doing so, prevents and treats a variety of adult illnesses and diseases, and because of its massaging effects, helps maintain and improve health.

BACKGROUND OF THE INVENTION

Recently, there has been much research and many reports on the benefits of artificially projecting far infrared rays, anions, etc. to specified areas on the body. The research and reports indicate that these procedures can promote health and can be efficacious in the prevention and treatment of a variety of adult illnesses.

Because of the results of such research, a large variety of pressure devices and health-aid instruments, designed with similar purposes as the pressure devices, have been devised. These health instruments are being used by a large number of people.

Examples of such devices are pressure instruments that use far infrared rays and massage devices that use anions.

However, the above pressure and massage devices have, for the most part, only a single function offering only a single effect or healthy benefit to the user. Therefore, a large number of different devices must be purchased and a great deal of time must be used if the user wants to attain more than one health effect.

In addition, when using the prior art devices, a large amount of the far infrared rays and anions accumulate on the skin surface and can not penetrate to the desired subcutaneous depth.

As a result, the prior art devices can not attain the beneficial health results that they were designed for, and, therefore, succeed only in wasting time and expense.

SUMMARY

The present invention has been made in an effort to solve the above problems.

It is an object of the present invention to provide a finger-pressure functioning health-aid instrument for improving circulation which uses far infrared rays, anions and magnetic force rays, derived from a variety of material that are known to be beneficial to health, and allows for the projection and accumulation of these to a desired area and depth.

To achieve the above object, the present invention provides a pressure device for improving circulation including a cylindrical body and a lower cap. The body has a space portion formed inside. The lower cap is inserted in the lower part of the body and has a space portion formed inside. The lower cap has a guide portion formed to be communicable with the outside. A negative ion discharge element is fixed in the upper part of the space portion of the lower cap. A bio-ceramic for emitting far infrared rays. A germanium compound is formed layered above the bio-ceramic. A permanent magnet is fixed under the negative ion discharge element and a pressure member is fixed contacting the lower face of the permanent magnet, and which contacts directly with the skin in the desired treatment area and projects anions and emitting rays.

DESCRIPTION

Preferred embodiments of the present invention will now be described in detail with reference to the accompanying drawings.

Figure 1:
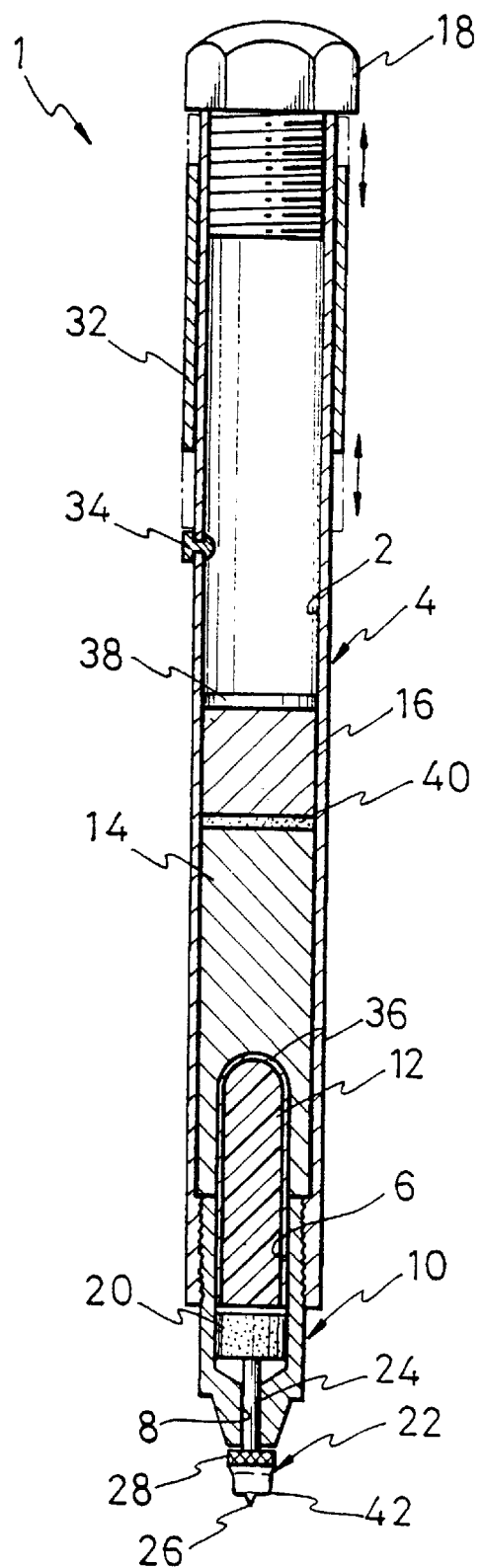
FIG. 1 is a longitudinal sectional view illustrating a finger-pressure functioning health-aid instrument for improving circulation in accordance with a preferred embodiment of the present invention.
Figure 2:
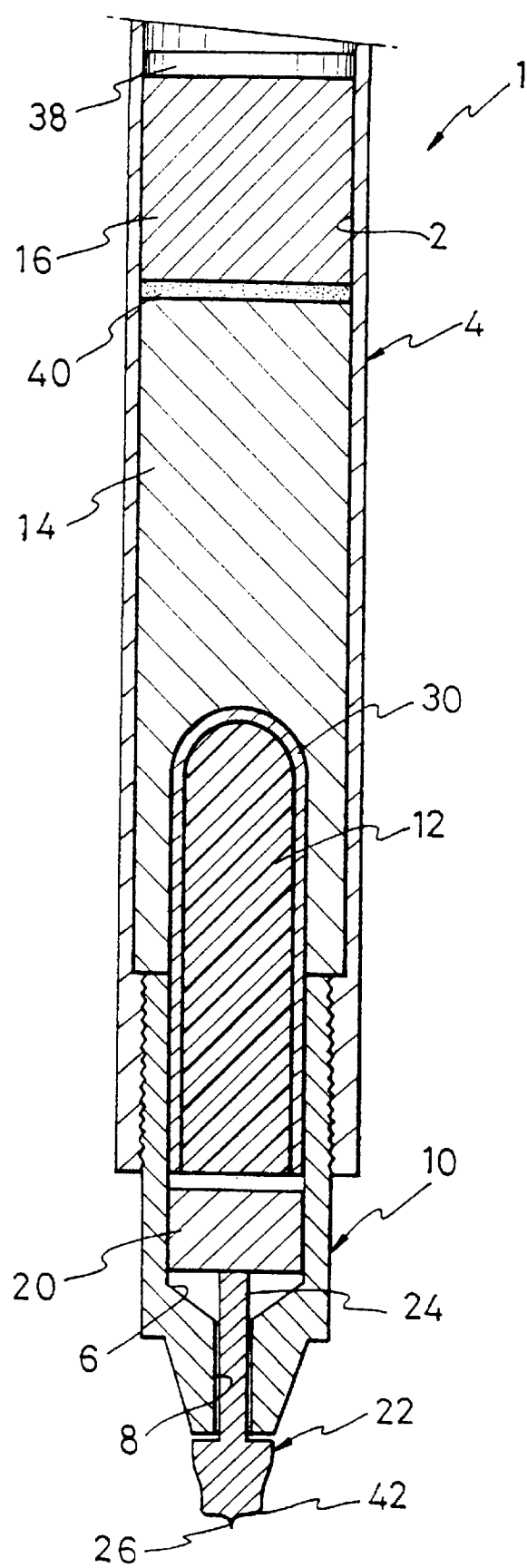
FIG. 2 is a partly enlarged sectional view of the instrument depicted in FIG. 1.
Figure 3:
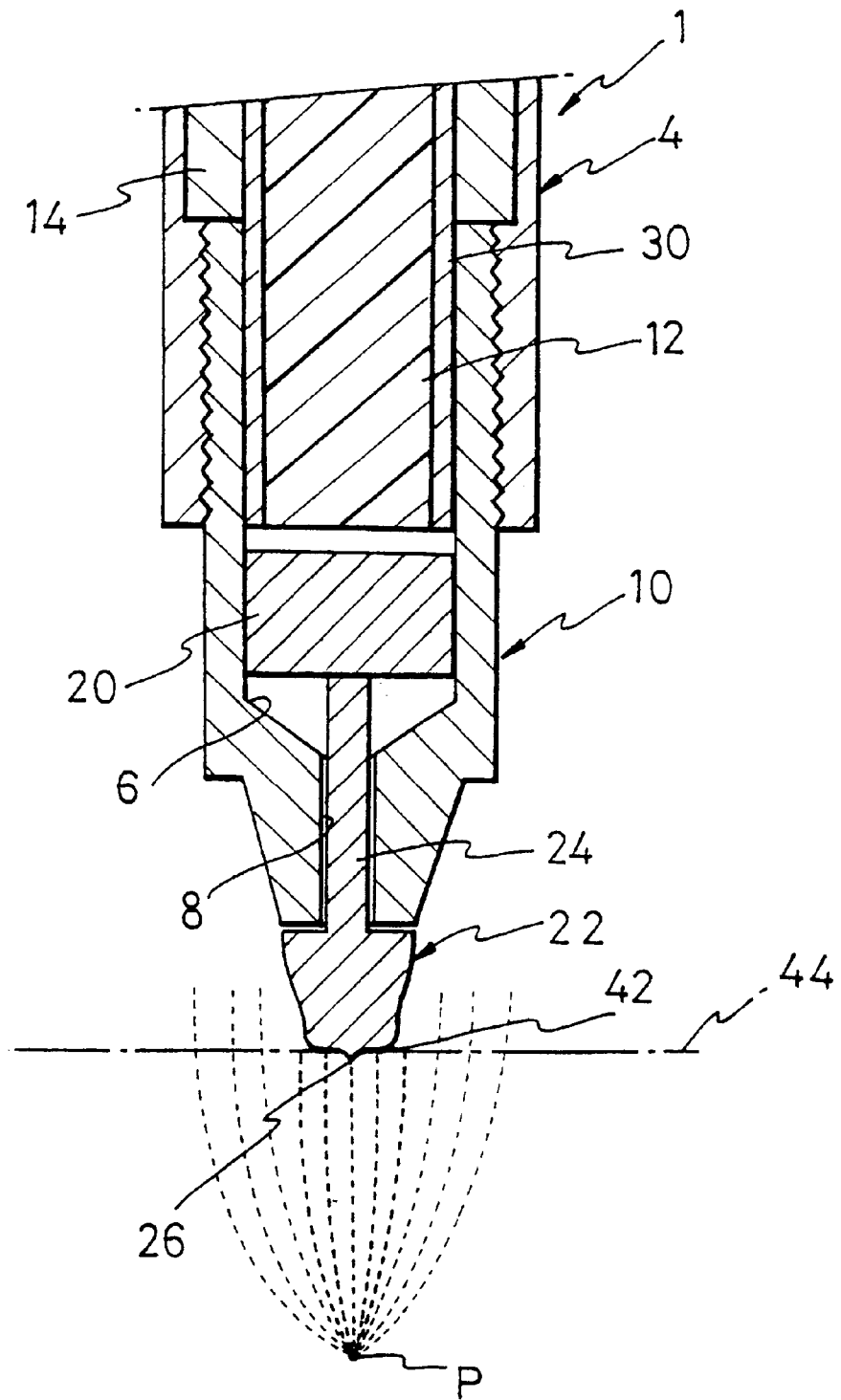
FIG. 3 is a partly enlarged sectional view showing a pressure device for improving circulation in a state where it is being used in accordance with a preferred embodiment of the present invention.

Referring to FIGS. 1–3, a finger-pressure functioning health-aid instrument 1 of the present invention includes a cylindrical body 4 having a space portion 2 formed on the inside of the body 4; and a lower cap 10, fixed to the lower part of the body 4, having a space portion 6, in which a guide portion 8 is formed communicable with the exterior of the body.

A negative ion discharge element 12, which emits anions, is formed in the upper part of the space part 6 of the lower cap 10. A permanent magnet 20, which emits magnetic force rays that stimulate blood flow, is fixed under the negative ion element 12.

A bio-ceramic 14, discharging far infrared rays that promote circulation, is formed in the space portion 2 of the body 4. The bio-ceramic 14 surrounds the upper part of the negative ion discharge element 12.

Also, a housing 36, which has an opening on its lower side, is fixed surrounding the outside of the negative ion discharge element 12. The housing 36 separates the negative ion discharge element 12 from the bio-ceramic 14.

A germanium compound 16 is formed in the space portion 2 of the body. The germanium compound 16 is excellent for the prevention of dermatological aging, the eradication of infectious bacteria, has anti-cancer effects, cell strengthening effects, and is efficacious in strengthening and lengthening sexual organs.

In addition, a spacing plate 40 made of a plastic material is fixed between and separating the germanium compound 16 and bio-ceramic 14.

A shielding plate 38 is fixed above the germanium compound 16 in the spacing portion 2 of the body 4. The shielding plate 38 reflects and sends downward the anions and far infrared rays that emit upward toward the germanium compound 16.

A control tool 32 is inserted in the upper, outside part of the body 4 which serves as a handle and allows the control of the instrument 1 when applying pressure. A stopper 34 is formed in the body 4 below the control tool 32 which limits the sphere of movement of the control tool 32.

Also, an upper portion cap 18 is inserted in the upper part of the body 4, the inserted portion of the upper portion cap 18 being screw-shaped. The upper portion cap 18, to prevent the control tool 32 from separating from the body 4, is formed having a diameter in its upper part slightly larger than that of the body 4.

A pressure member 22 is fixed in the lower side of the permanent magnet 20, which is disposed inside the lower cap 10. The pressure member 22 is fixed protruding out the lower part of the lower cap 10 making direct contact with the skin to allow the projecting of anions and emitting rays on the skin.

The pressure member 22, located outside the lower cap 10, has a guide rod 24 fixed extending upward. The guide rod 24 does not become separated from the lower cap 10 because of the permanent magnet 20, and so as to allow the pressure operation, has absorptive force by the magnetic force of the permanent magnet 20.

Furthermore, the pressure member 22 includes a sharp tip portion 26 in its lower part and a display portion 28 fixed above the pressure member 22 which displays an N pole or S pole.

It is preferable that the portion of the surface of the pressure member 22 that contacts the skin is plated with gold so as to prevent an allergic reaction. An end portion 42 is formed on the pressure member 22 so as to prevent too much pressure from being applied to the skin.

It is also preferable that the body 4 is made of a material that reflects anions and emitting rays so that these only are discharged on to the skin through the pressure member 22 and not projected outside the body.

The following is the operation of the instrument 1 structured as in the above.

First, the tip portion 26 of the circulation pressure device 1 is made to contact with the skin.

Here, the amount of pressure is controlled by the control tool 32. If the control tool 32 is grasped and the upper cap 18 is pushed while the body 4 is moved downward, pressure is applied to the skin.

The tip portion 26 stimulates certain areas of the body, improving circulation and providing Chinese acupuncture effects. The end portion is formed on the pressure member 22 such that excess pressure is not applied to the skin.

Furthermore, the emitting rays and anions projected from the germanium compound 16, the bio-ceramic 14, and the negative ion discharge element 12 are reflected by the shielding plate 38 and the body 4 and flow down to the lower cap 10.

The emitting rays are projected to the outside through the guide shaft 8 and emitted directly on to the skin.

The anions collected at the lower cap 10 are discharged on to the skin through the pressure member 22, and by the magnetic rays of the permanent magnet 20, are accumulated and projected deep into the skin.

FIG. 3 illustrates how the anions are accumulated by the magnetic rays and are projected to a focal point (P). As illustrated, the magnetic rays and anions are accumulated and projected to the focal point (P).

Because the anions are incited and projected deep into the skin by the magnetic rays, increased effects are received from the anions.

Other embodiments of the invention will be apparent to the skilled in the art from consideration of the specification and practice of the invention disclosed herein. It is intended that the specification and examples be considered as exemplary only, with the true scope and spirit of the invention being indicated by the following claims.

What is claimed is:

1. A finger-pressure functioning health-aid instrument for improving blood circulation of a human body, comprising:

a cylindrical body;

a lower cap, inserted in a lower end of the body, the lower cap being provided with a guide passage communicable with an outside;

means, disposed within the body, for discharging anions;

means, disposed within the cylindrical body, for emitting far infrared rays; and pressure applying means including a collecting member for collecting anions discharged from the anions discharging means and far infrared rays emitted from the far infrared rays emitting means; and a pressure member connected to the collecting member, the pressure member contacting directly with the skin in a desired treatment area while projecting collected anions and far infrared rays.

2. A finger-pressure functioning health-aid instrument according to claim 1, wherein the far infrared rays emitting means comprises a bio-ceramic material.

3. A finger-pressure functioning health-aid instrument according to claim 1, wherein the collecting member is connected to the pressure member by a guide shaft disposed through the guide passage, a first end of the guide shaft being disposed inside the instrument and a second end of the guide shaft being disposed outside of the instrument, and wherein the collecting member is attached on the first end and the pressure member is attached on the second end.

4. A finger-pressure functioning health-aid instrument according to claim 3, wherein the pressure member comprises a tip portion and a sharp end.

5. A finger-pressure functioning health-aid instrument according to claim 1 further comprising an upper cap having a larger diameter than that of the body and fixed in an upper end of the body.

6. A finger-pressure functioning health-aid instrument according to claim 5 further comprising a control tool which is sliderably inserted in an outer circumference of the body between the upper cap and a stopper formed in the outer circumference of the body to limit the movement of the control tool, the control tool acting as a handle to allow the control of pressure.

7. A finger-pressure functioning health-aid instrument according to claim 1, wherein the far infrared rays emitting means is provided with a groove and a portion of the anion discharge means is fitted into the groove, and wherein a separating member is formed between the anion discharge means and the far infrared rays emitting means.

8. A finger-pressure functioning health-aid instrument according to claim 1, wherein the pressure member is plated with gold to prevent an allergic reaction when applied to a skin.

9. A finger-pressure functioning health-aid instrument according to claim 1, an end portion is formed in the pressure member to prevent excessive pressure from being applied to a skin.

* * * * *